United States Patent [19]
Koller et al.

[11] 3,969,346
[45] July 13, 1976

[54] NAPHTHOLACTAMCARBINOLS COLOR FORMERS, THEIR MANUFACTURE AND USE IN PRESSURE-SENSITIVE OR THERMOREACTIVE RECORDING MATERIAL

[75] Inventors: Stefan Koller, Ramlinsburg; Jean Claude Petitpierre, Kaiseraugst, both of Switzerland

[73] Assignee: Ciba-Geigy Corporation, Ardsley, N.Y.

[22] Filed: July 3, 1973

[21] Appl. No.: 376,256

[30] Foreign Application Priority Data
July 7, 1972    Switzerland...................... 10207/72

[52] U.S. Cl.......................... 260/240 E; 260/240.9; 260/244 R; 260/288 R; 260/293.59; 260/310 R; 260/313.1; 260/315; 260/326.13 R; 260/326.15; 260/326.5 B; 282/27.5; 428/488
[51] Int. Cl.²...................................... C07D 209/90
[58] Field of Search.......... 260/319.1, 313.1, 240 E, 260/240.9, 326.5 B, 315, 310 R, 326.13 R, 326.15, 240 F

[56] References Cited
UNITED STATES PATENTS

| | | | |
|---|---|---|---|
| 3,362,953 | 1/1968 | Brack | 260/240 E |
| 3,513,173 | 5/1970 | Mix | 260/310 |

FOREIGN PATENTS OR APPLICATIONS

| | | | |
|---|---|---|---|
| 473,196 | 7/1969 | Switzerland | 260/326.5 B |
| 116,643 | 6/1958 | U.S.S.R. | 260/313.1 |
| 281,257 | 9/1928 | United Kingdom | 260/326.5 B |

OTHER PUBLICATIONS

Zaitsev et al., Chemical Abstracts vol. 70, abst. No. 53,407q, (1969), (abst. of Saitsev et al., Ukr. Khim. Zh. vol. 34, pp. 1003 to 1009, 1968).
Chemical Abstracts, 8th Collective Subject Index, 1967–1971, p. 3981S.
Zaitsev et al., Ukr. Khim. Zh., vol. 34, pp. 1003–1009, (1968).

*Primary Examiner*—John D. Randolph
*Attorney, Agent, or Firm*—Joseph G. Kolodny; Edward McC. Roberts; Prabodh I. Almaula

[57] ABSTRACT

The present invention relates to naphtholactamcarbinols, which may be used as color formers in pressure-sensitive or thermoreactive recording material.

6 Claims, No Drawings

NAPHTHOLACTAMCARBINOLS COLOR FORMERS, THEIR MANUFACTURE AND USE IN PRESSURE-SENSITIVE OR THERMOREACTIVE RECORDING MATERIAL

The present application relates to new compounds suitable for use as colour formers, of the formula

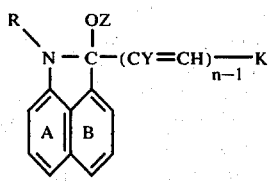

$$(1)$$

wherein R denotes an optionally substituted alkyl, cycloalkyl, aryl or aralkyl radical, K is the radical of a compound capable of coupling, Z is lower alkyl or preferably hydrogen, Y is lower alkyl, nitrile or preferably hydrogen and n is 1 or 2 and wherein the rings A and B are optionally substituted.

The radical R can be, for example, one of the following groups: $C_1$–$C_6$-alkyl, cyclohexyl, phenyl, benzyl or β-phenylethyl. These groups, especially the alkyl radicals, can be substituted by halogen, low molecular alkoxy, dialkylamino, alkanoyl, alkanoylamino, carbalkoxy, alkoxycarbonylamino or alkylarylamino.

Possible compounds capable of coupling are above all disubstituted anilines and naphthylamines, indoles, phenol-ethers and naphthol-ethers, especially low molecular alkyl-ethers, as well as phenylpyrazolines, tetrahydroquinolines, tetrahydrocarbazoles and phenoxazines.

The rings A and B of the naphtholactam can carry nonionic substituents or can be unsubstituted. Examples of suitable substituents are: halogen, especially chlorine and bromine; low molecular alkyl, alkoxy, dialkylamino or alkylarylamino groups, such as methyl, ethyl, butyl, methoxy, ethoxy, dimethylamino, methylethylamino or ethylphenylamino; acyl and acylamino radicals, especially low molecular alkanoyl, alkanoylamino, alkoxycarbonyl, alkoxycarbonylamino, alkylated carbonamido and ureido groups, such as, for example, acetyl, acetylamino, benzoylamino, ethoxycarbonylamino or dimethylaminocarbonylamino, sulphonyl or aminosulphonyl radicals, especially alkylsulphonyl, arylsulphonyl or dialkylaminosulphonyl radicals, such as methylsulphonyl, phenylsulphonyl or dimethylaminosulphonyl. By "low molecular" there are here generally meant radicals with 1 to 4 C atoms.

A group of preferred compounds are those of the formula

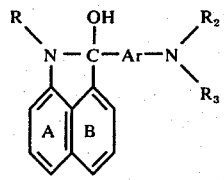

$$(2)$$

wherein Ar is an aromatic radical and $R_2$ and $R_3$ each denote an optionally substituted alkyl, aryl, cycloalkyl or aralkyl group and R, A and B have the same meaning as above.

Preferably, in this formula, Ar is an unsubstituted phenyl radical or a phenyl radical substituted by low molecular alkyl or alkoxy groups. $R_2$ and $R_3$ are above all low molecular alkyl radicals or radicals of the benzene series and can be substituted by the following groups: halogen, nitrile, $C_1$–$C_4$-alkoxy, $C_1$–$C_4$-alkyl, low molecular dialkylamino or alkylarylamino, for example methylphenylamino, or acyl groups, such as $C_1$–$C_4$-alkanoyl, benzoyl or carbalkoxy. Further suitable radicals $R_2$ and $R_3$ are cyclohexyl, cyclopentyl, benzyl and β-phenylethyl. Furthermore, $R_2$ and $R_3$ can be linked to one another and can form part of a saturated heterocyclic ring system, say of a pyrrolidine or piperidine ring.

A further group of preferred compounds are those of the formula

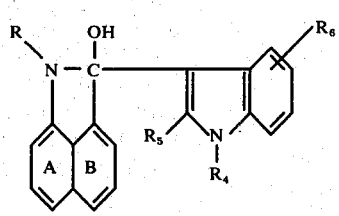

$$(3)$$

wherein $R_4$ is a hydrogen atom, an aryl or aralkyl radical or an optionally substituted alkyl or alkenyl radical, $R_5$ denotes hydrogen or an aryl or low molecular alkyl radical and $R_6$ represents low molecular alkyl or alkoxy groups or halogen, and R, A and B have the same meaning as above. $R_4$ is, in particular, a phenyl, tolyl, benzyl, β-phenylethyl or $C_1$–$C_{18}$-alkyl or alkenyl radical which is optionally substituted by chlorine, nitrile or low molecular carbalkoxy or alkylcarbonamido groups. R and the aromatic rings A and B have the same meaning as indicated above.

The compounds according to the invention are manufactured by treating a naphtholactam dyestuff of the formula

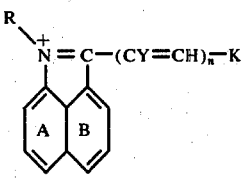

$$(4)$$

wherein R, n, Y and K have the indicated meaning and the rings A and B can optionally be substituted, with a compound which provides alkoxy ions or preferably hydroxyl ions. Appropriately, the reaction is carried out in an aqueous medium and dilute alkaline solutions of Na ethanolate or above all sodium hydroxide solutions or potassium hydroxide solutions are used. The naphtholactam dyestuffs of the formula (4) used as starting compounds are manufactured in a known manner by condensation of a coupling component with a 1,8-naphtholactam of the formula -continued

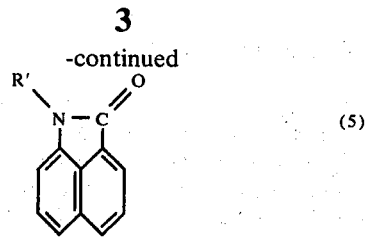

(5)

wherein R' denotes hydrogen or an optionally substituted alkyl, cycloalkyl, aryl or aralkyl radical. If R' is hydrogen, the products which result must subsequently still be quaternised. The manufacture of such naphtholactam dyestuffs is described, for example, in German Pat. Specifications Nos. 1,1920,126 (sic), 1,190,126b and 1,165,790, which also give examples of suitable starting compounds of the formula (5). By way of supplement of the data given there, the following should be mentioned as further examples: N-methyl-2-ethylnaphtholactam-1,8, N-methyl-2-phenyl-naphtholactam-1,8, N-ethyl-4-methylphenyl-amino-naphtholactam-1,8, N-ethyl-4-(N',N'-bisethoxycarbonylamino)-naphtholactam-1,8, N-methyl-4-propionyl-naphtholactam-1,8, N-methyl-4-methylsulphonyl-naphtholactam-1,8, N-methyl-4-phenylsulphonyl-naphtholactam-1,8 or N-methyl-4-diethylaminosulphonyl-naphtholactam-1,8.

The patent specifications mentioned also indicate a selection of suitable coupling components of the aniline series. Additionally to the compounds mentioned there, the following coupling components, for example, are also of interest for the colour formers according to the invention: 1-methylindole, 1-ethylindole, 1-methyl-2-phenylindole, 1,2-dimethylindole, 1-propyl-2-methylindole, 1-ethyl-2-methyl-5-methoxyindole, 1-butylindole, 1-pentyl-2-methylindole, 1-β-cyanoethyl-2-methylindole, 1-benzyl-2-methylindole, 1-octyl-2-methylindole, 1-dodecyl-2-methylindole, 1-stearyl-2-methylindole, 1-methyl-7-ethylindole, 1-methyl-5-ethoxyindole, 1-methyl-5-chloroindole, 1-methyl-5-bromoindole, 1-methyl-7-chloroindole, 7-ethylindole, 1-(2'-carbethoxy)-ethyl-2-methylindole, 1-(2'-N-methylcarbonamido)-ethyl-2-methylindole, 1-allyl-2-methylindole, methoxybenzene, 1,3-dimethoxybenzene, 1-methyl-3-methoxybenzene, 1-phenyl-3,5,5-trimethylpyrazoline, 1-methoxynaphthalene, 1-dimethylaminonaphthalene, bis-(β-cyanoethyl)-aniline, N-ethyl-N-β-phenylethylaniline or N-ethyl-N-β-phenylcarbonyloxyethyl-aniline, N-ethyl-1,2,3,4-tetrahydrocarbazole, N-methylphenoxazine or 1-ethyl-3-hydroxy-7-methyl-1,2,3,4-tetrahydroquinoline.

The products according to the invention are suitable for use as colour formers, for example in pressure-sensitive or thermo-reactive recording material.

Pressure-sensitive copying material preferably has at least a pair of sheets and contains at least one colour former of the formula (1), in an organic solvent and preferably in micro-capsules which can be broken open by pressure, and a solid electron acceptor, the colour former being able to produce a coloured mark, on contact with the solid electron acceptor, at those points at which pressure is exerted on the copying material.

In the colour formers employed in the pressure-sensitive copying materials, premature activity is prevented by separating them from the development components. As a rule this is done by incorporating the colour formers into foamlike, spongy or honeycomb-like structures. However, preferably the colour formers are encapsulated in micro-capsules.

If the colourless colour formers of the formula (1) are dissolved in an organic solvent, they can be subjected to a micro-encapsulation process and then be used for the manufacture of pressure-sensitive papers. If the capsules are broken open by the pressure of, for example, a pencil, and the colour former solution then transferred onto the adjacent sheet, which is coated with a substrate which can act as an electron acceptor, a coloured image is formed. This new colour thus results from a naphtholactam dyestuff which absorbs in the visible range of the electromagnetic spectrum.

The manufacture of micro-capsules or the encapsulation by micro-capsules have long been known to those skilled in the art. Well-known processes are described, for example, in U.S. Pat. Nos. 2,183,053, 2,800,457, 2,800,458, 3,265,630, 2,964,331, 3,418,656, 3,418,250, 3,016,308, 3,424,827, 3,427,250, 3,405,071, 3,171,878 and 2,797,201. Further processes are described in British Pat. Nos. 989,264 and above all 1,156,725. All these processes and all other known processes are suitable for encapsulating the colour formers used according to the invention.

Preferably, the colour formers are encapsulated in the form of their organic solutions. Suitable solvents are preferably non-volatile, such as the polyhalogenated diphenyls, such as trichlorodiphenyl and its mixtures with liquid paraffin, tricresyl phosphate, di-n-butyl phthalate, dioctyl phthalate, trichlorobenzene, nitrobenzene, trichloroethyl phosphate, petroleum ether, hydrocarbon oils such as paraffin, condensed derivatives of diphenyl or triphenyl, chlorinated and hydrogenated condensed aromatic hydrocarbon compounds and the like. The walls of the micro-capsules are preferably uniformly precipitated by coacervation forces around the droplets of the colour formers solution, the material from which the micro-capsules are formed being gelatine as is described, for example, in U.S. Pat. No. 2,800,457.

On the other hand, the capsules can also preferably be formed from aminoplast or modified aminoplasts by polycondensation, as described in British Pat. Nos. 989,264 and 1,156,725.

The colour formers of the formula (1) are appropriately separately introduced into micro-capsules and are then brought into contact with an electron acceptor applied to the receiving sheet.

In a preferred embodiment, the encapsulated colour formers is applied as a coating to the rear of a transfer sheet whilst the electron acceptor is applied to the front of a receiving sheet.

Another interesting system is that wherein the encapsulated colour formers is applied to the rear of the transfer sheet and the electron acceptor to the front of the receiving sheet.

According to another embodiment, the colour formers of the formula (1) are encapsulated together with one or more other known colour formers such as Crystal Violet lactone or Indoyl Red.

The preferred colour reaction component which serves as the electron acceptor is attapulgite or an acid phenolic resin. These electron acceptors are preferably coated onto the front of the receiving sheet.

The micro-capsules containing the colour formers of the formula (1) are used for the manufacture of pressure-sensitive copying materials of the most diverse known types, such as the so-called "chemical transfer", "chemical self-contained" and "monoform" papers. The various systems differ essentially in the arrangement of the capsules, the colour reagents and the carrier material.

The micro-capsules can be provided in an undercoat of the upper sheet and the colour reactor, that is to say the electron acceptor can be provided in the upper layer of the lower sheet. However, the constituents can also be introduced into the paper pulp. Such systems are called "chemical transfer" systems.

Another arrangement of the constituents consists of the micro-capsules containing the colour former and the electron acceptor being provided in or on the same sheet as one or two separate layers, or in the paper pulp. Such systems are described as "chemical self-contained" systems.

Such pressure-sensitive copying materials are described, for example, in U.S. Pat. Nos. 3,516,846, 2,730,457, 2,932,582, 3,427,180, 3,418,250 and 3,418,656. Further systems are described in British Pat. Nos. 1,042,597, 1,042,598, 1,042,596, 1,042,599, 1,053,935 and 1,517,650. The micro-capsules containing the colour formers of the general formula (1) can be employed in conjunction with each of these systems or other systems.

The capsules are preferably fixed to the carrier by means of a suitable adhesive. Since paper is the preferred carrier material, such adhesives are in the main paper coating agents such as, for example, gum arabic, polyvinyl alcohol, hydroxyethylcellulose, casein, methylcellulose or dextrin.

In the present description, the term "paper" not only includes normal paper of cellulose fibres, but also types of paper in which the cellulose fibres are partially or completely replaced by synthetic fibres of polymers.

The heat-sensitive recording material preferably contains in at least one layer on a carrier at least one colour former of the formula (1) and an electron acceptor in a fusible, preferably film-forming binder.

The heat-sensitive recording material is recording material or recording paper which is suitable both for simple recording purposes and for use as a copying paper or reprography paper by the thermograph process. The recording can be carried out in information recording instruments, such as facsimile or telegraph recording instruments, telex typewriters or remote-operated recording measuring instruments, electronic calculators, various measuring devices and copying machines or also mechanically or manually by means of hot writing instruments.

The recording material thus contains, at least the colourless colour former as the actual recording component, an electron acceptor which is capable of developing the colour former to give a dyestuff, and a binder.

The material can be built up in such a way that the colour former is present dissolved or dispersed in the binder in one layer, whilst the dyestuff developer or electron acceptor is present dissolved or dispersed in a second layer. Another possibility is that both the colour former and the dyestuff developer are presents dispersed in the same layer. If, in that case, the binder is caused to soften by application of heat at a given point, the dyestuff develops at this point and an image-wise recording results, since contact is made between the colour former and the dyestuff developer at the warmed point.

The dyestuff developer preferably consists of Lewis acids, that is to say so-called attapulgite, acid phenolic compounds or resins or organic acids. For formation of the dyestuff it is desirable that the electron acceptor in question should be solid at room temperature and melt or volatilise above about 50°C. Examples of phenolic compounds are; 4-tert.-butylphenol, 4-phenylphenol, 4-dihydroxydiphenyl oxide, α-naphthol, 4-hydroxybenzoic acid methyl ester, β-naphthol, 4-hydroxyacetophenol, 4-tert.-octylpyrocatechol, 2,2'-dihydroxydiphenyl, 2,2'-methylene-bis-(4-chlorophenol), 4,4'-isopropylidenediphenol (bisphenol A), 4,4'-isopropylidene-bis-(2-chlorophenol), 4,4'-isopropylidene-bis-(2,6-dibromophenol), 4,4'-isopropylidene-bis-(2,6-dichlorophenol), 4,4'-isopropylidene-bis-(2-methylphenol), 4,4'-sec-isobutylidenediphenol, 4,4'-cyclohexylidenediphenol, 2,2'-thio-bis-(4,6-dichlorophenol), hydroquinone, pyrogallol, phloroglucinol and phloroglucinol-carboxylic acid.

Examples of suitable organic acids are: p-, m- and o-hydroxybenzoic acid, boric acid, tartaric acid, oxalic acid, maleic acid, citraconic acid, succinic acid, gallic acid, 1-hydroxy-2-naphthenic acid or 2-hydroxy-p-toluic acid.

Preferably, products which are water-soluble are used as fusible film-forming binders, since the colour former and the dyestuff developer are water-insoluble. The binder should be capable of dispersing and fixing the colour former and dyestuff developer at room temperature so that these are contained in a non-coherent form in the material. On application of heat, the binder softens or melts, which allows the colour former to come into contact with the dyestuff developer, and a dyestuff is formed.

Possible binders which are water-soluble or at least swellable in water are, for example: polyvinyl alcohols, polyacrylic acid, hydroxyethylcellulose, polyacrylamide, carboxymethylcellulose, methoxycellulose, polyvinylpyrrolidone, gelatine or starch. Where the colour former and the dyestuff developer are applied in two different layers it is also possible to employ water-insoluble binders, that is to say binders which are soluble in non-polar or weakly polar organic solvents. Examples are natural rubber, synthetic rubbers, chlorinated rubbers, alkyd resins, polystyrene, styrene-butadien copolymers, polymethyl methacrylates, ethylcellulose, nitrocellulose or polyvinylcarbazole.

Preferably, however, water-soluble binders are used with colour formers and dyestuff developers in one layer.

The coatings of the recording material can contain yet further additives. In order to improve the degree of whiteness and the printability of the recording paper and to prevent the hot writing tip from becoming stuck it is possible to employ, for example, talc, titanium dioxide, zinc oxide or calcium carbonate. In order to achieve dyestuff formation within a narrowly defined temperature it is furthermore possible to use urea, thiourea, acetanilide, phthalic anhydride or appropriate fusible substances which at the time that they themselves melt convert the dyestuff precursor and the dyestuff developer into the fused state.

In the examples which follow the parts, unless otherwise stated, denote parts by weight and the percentages denote percentages by weight.

EXAMPLE 1

11.1 parts of 1-methyl-2-phenylindole and 9.85 parts of N-ethyl-naphtholactam-(1,8), in 105 parts of o-dichlorobenzene, are warmed to 120°C. 10 parts of phosphorus oxychloride are added dropwise at this temperature. After the dropwise addition, the mixture is kept at 120°–125°C for a further 2 hours and is then allowed to cool, and the reaction mass is poured into 500 parts of water. After separating off the o-dichlorobenzene, a dyestuff solution which is coloured deep red is obtained. This is treated with 2 N sodium hydroxide solution at 50°C until the deep red colour has completely disappeared. The colourless carbinol which precipitates, of the formula

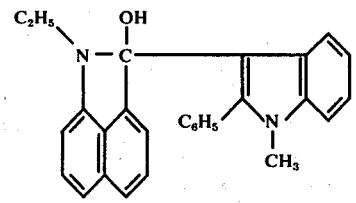

is filtered off and the filter residue is washed with water and dried in vacuo. On contact with Lewis acids or Bronsted acids the red colour is instantly regenerated.

EXAMPLE 2

13.8 parts of 4-bromo-N-ethyl-naphtholactam-(1,8) and 7.4 parts of diethylaniline are stirred together with 38 parts of phosphorus oxychloride for 15 hours at 80°C. The reaction mass is then poured onto 400 parts of ice and the pH-value is adjusted to 4 with concentrated ammonia solution. The deep blue dyestuff salt is then converted into the colourless water-insoluble carbinol by dropwise addition of 2 N sodium hydroxide solution. The carbinol is filtered off and the filter residue is well washed with water and dried in vacuo. With acids, the blue dyestuff is immediately regenerated.

EXAMPLES 3 to 42

The colour formers of the table which follows can be manufactured analogously to the description in Examples 1 and 2, and after acid development on the paper the colour shades indicated in the last column are produced.

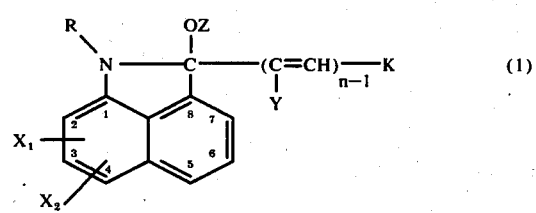

| Example No. | R | $X_1$ | $X_2$ | Z | Y | n | K | Colour shade after development |
|---|---|---|---|---|---|---|---|---|
| 3 | $H_3C-$ | H | H | H | — | 1 | —⌬—$N(CH_3)_2$ | violet |
| 4 | $H_3C-$ | 2-Br | 4-Br | H | — | 1 | " | reddish-tinged blue |
| 5 | $H_5C_2-$ | 4-$NO_2$ | H | H | — | 1 | " | blue |
| 6 | $H_3C-$ | 4-$SO_2N(CH_3)_2$ | H | H | — | 1 | " | blue |
| 7 | $H_3C-$ | 4-$NHCOCH_3$ | H | H | — | 1 | —⌬—N(CH$_3$)—⌬— | reddish-tinged blue |
| 8 | $H_3C-$ | 4-$SO_2CH_3$ | H | H | — | 1 | —⌬—$N(CH_3)_2$ | blue |
| 9 | $H_3C-$ | 4-$H_3CCO-$ | H | H | — | 1 | " | blue |
| 10 | $H_3C-$ | 4-NHCONH— | H | H | — | 1 | " | reddish-tinged blue |
| 11 | $NC-C_2H_4-$ | H | H | H | — | 1 | " | reddish-tinged blue |
| 12 | $Cl-C_2H_4-$ | 4-Br | H | H | — | 1 | —⌬—N(CH$_3$)—⌬— | reddish-tinged blue |
| 13 | $C_6H_5CH_2-$ | 2-$H_3C-$ | H | H | — | 1 | —⌬—$N(C_2H_5)_2$ | violet |
| 14 | $H_3CNHCOC_2H_4-$ | H | H | H | — | 1 | —⌬—$N(CH_3)_2$ | violet |
| 15 | $H_3COC_2H_4-$ | 2-$C_2H_5$ | H | H | — | 1 | " | violet |
| 16 | $H_2NCOC_2H_4-$ | H | H | H | — | 1 | " | violet |
| 17 | $CH_3-$ | H | H | H | H | 2 | " | greenish-tinged blue |
| 18 | $C_3H_7-$ | 4-Cl | H | H | H | 2 | —⌬(CH$_3$)—N($C_2H_4Cl$)($C_2H_4CN$) | blue |

-continued

| Example No. | R | $X_1$ | $X_2$ | Z | Y | n | K | Colour shade after development |
|---|---|---|---|---|---|---|---|---|
| 19 | $C_2H_5-$ | 4-$OCH_3$ | H | H | H | 2 | 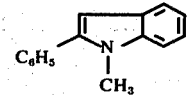 | reddish-tinged blue |
| 20 | $H_3C$ | H | H | H | $-CH_3$ | 2 | 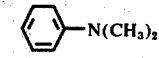 | greenish-tinged blue |
| 21 | $H_3C$ | H | H | H | $HC\begin{smallmatrix}CH_3\\CH_3\end{smallmatrix}$ | 2 | " | greenish-tinged blue |
| 22 | $H_3C$ | H | H | H | $-CN$ | 2 | " | greenish-tinged blue |
| 23 | $-C_2H_5$ | H | H | $H_3C-$ | — | 1 | " | violet |
| 24 | $-C_2H_5$ | H | H | $C_2H_5-$ | — | 1 | " | violet |
| 25 | $C_2H_5-$ | H | H | H | — | 1 | 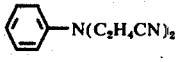 | bluish-tinged red |
| 26 | $C_2H_5-$ | 4-Br | H | H | — | 1 | 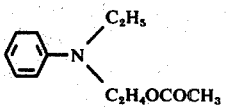 | violet |
| 27 | $C_2H_5-$ | H | H | H | — | 1 | 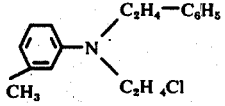 | reddish-tinged violet |
| 28 | $C_2H_5-$ | H | H | H | — | 1 | 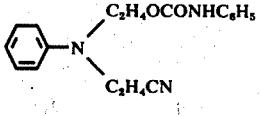 | bluish-tinged red |
| 29 | $C_2H_5-$ | 4-$SO_2NHCH_3$ | H | H | — | 1 | 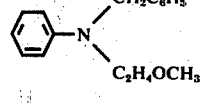 | blue |
| 30 | $H_3C-$ | H | H | H | — | 1 | 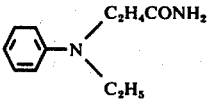 | reddish-tinged violet |
| 31 | $H_3C-$ | 4-Br | H | H | — | 1 | 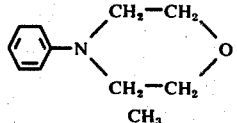 | reddish-tinged blue |
| 32 | $C_2H_5-$ | H-Br | H | H | — | 1 | 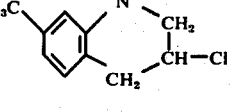 | blue |
| 33 | $C_2H_5$ | 4-Cl | 2-Cl | H | — | 1 | 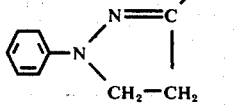 | greenish-tinged blue |

-continued
| Example No. | R | $X_1$ | $X_2$ | Z | Y | n | K | Colour shade after development |
|---|---|---|---|---|---|---|---|---|
| 34 | $C_2H_5-$ | H | H | H | — | 1 | 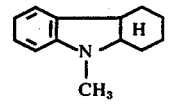 | blue |
| 35 | $H_3C-$ | 2-$C_2H_5$ | H | H | — | 1 | 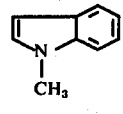 | yellow-tinged red |
| 36 | $C_2H_5-$ | H | H | H | — | 1 | 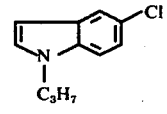 | yellow-tinged red |
| 37 | $C_2H_5-$ | H | H | H | — | 1 | 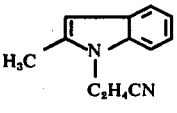 | yellow-tinged red |
| 38 | $NCC_2H_4-$ | 4-Br | H | H | — | 1 | 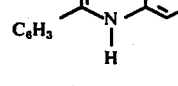 | red |
| 39 | $C_2H_5-$ | H | H | H | — | 1 | 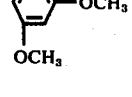 | orange |
| 40 | $C_2H_5-$ | H | H | H | — | 1 | 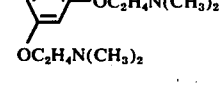 | reddish-tinged yellow |
| 41 | $H_3C-$ | 4-Br | H | H | — | 1 | 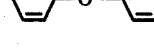 | orange |
| 42 | $H_3C-$ | H | H | H | — | 1 | 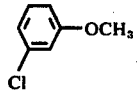 | orange |

EXAMPLE 43

A solution of 3 g of the colour former according to Example 1, in 100 g of trichlorodiphenyl, is emulsified in a solution of 12 g of gelatine in 88 g of water at 50°C. A solution of 12 g of gum arabic in 88 g of water is then added at 50°C and thereafter 200 ml of water are added at 45 to 50°C. The resulting emulsion is then poured into 600 g of a mixture of ice and water and is stirred until the temperature is 20°C. Sheets of paper are then coated with the mixture and dried. A second sheet of paper is coated with attapulgite. The first sheet and the sheet coated with attapulgite are placed on top of one another with the coatings adjoining. Writing under pressure on the first sheet produces an exact copy on the sheet coated with clay. The copy is red in colour and develops within 2 minutes. Instead of the colour former according to Example 1, the colour formers of Examples 2 to 42 can be employed, with similar success.

EXAMPLE 44 a. 7 g of the colour former according to Example 1, 300 g of a 10% strength aqueous polyvinyl alcohol solution and 130 ml of water are ground together for one hour so that an aqueous preparation of viscosity 23 to 28 centipoise is produced. The diameter of the colour former particles is about 1 to 3 $\mu$.

b. Simultaneously, 70 g of 4,4'-isopropylidenediphenol and 300 g of 10% strength aqueous polyvinyl alcohol solution are ground with 130 ml of water for one hour. After grinding, the particles still have a diameter of 1 to 3 $\mu$.

c. 6 g of the colour former dispersion and 134 g of the phenol dispersion are now mixed and applied to a sheet of paper, whereby a coating of 0.3 to 0.45 g/cm² is produced.

The dried paper is coated with 3% of dyestuff precursor, 67% of developer and 30% of polyvinyl alcohol.

The coated paper is now placed, with the coated side downwards, on an untreated paper surface. Marks can now be made with a hot writing instrument on the top surface of the two-sheet system, and these marks are faithfully transferred onto the second, lower, sheet.

Instead of the colour former according to Example 1, the remaining dyestuff precursors of Examples 2 to 42 can be used with similar success.

What we claim is:

1. Color former of the formula

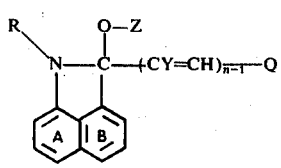

in which R is alkyl with 1 to 6 carbon atoms, cyclohexyl, phenyl, benzyl, 2-phenylethyl or alkyl with 1 to 6 carbon atoms substituted by halogen or alkoxy with 1 to 4 carbon atoms, Z is hydrogen or alkyl with 1 to 4 carbon atoms, Y is alkyl with 1 to 4 carbon atoms, nitrile or hydrogen, $n$ is 1 or 2, Q is a radical of the formula

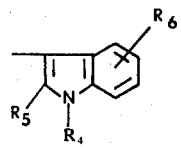

wherein $R_4$ is phenyl, tolyl, benzyl, 2-phenylethyl or alkyl or alkenyl with 1 to 18 carbon atoms or such a radical further substituted by chlorine, nitrile, carbalkoxy with 1 to 4 carbon atoms or alkylcarbonamido with 1 to 4 carbon atoms or $R_4$ is hydrogen; $R_5$ is hydrogen, phenyl or alkyl with 1 to 4 carbon atoms and $R_6$ is alkyl with 1 to 4 carbon atoms, alkoxy with 1 to 4 carbon atoms or halogen.

2. Color former of claim 1, of the formula

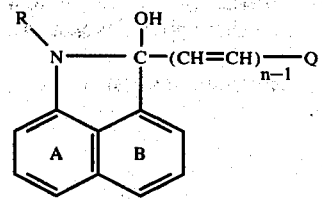

wherein R is alkyl with 1 to 6 carbon atoms, cyclohexyl, phenyl, benzyl, 2-phenylethyl or alkyl with 1 to 6 carbon atoms substituted by halogen or alkoxy with 1 to 4 carbon atoms.

3. Color former of claim 1, wherein Q is a radical of the formula

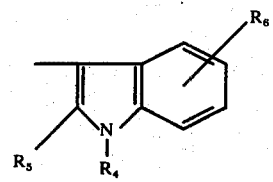

wherein $R_4$, $R_5$ and $R_6$ have the meaning defined in claim 1.

4. Color former of claim 1, of the formula

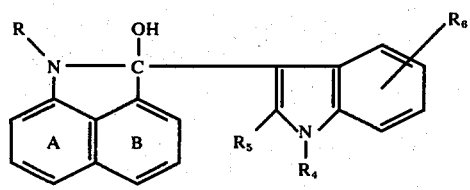

wherein R, $R_4$, $R_5$ and $R_6$ have the meaning defined in claim 1.

5. The colour former of claim 1, wherein R is ethyl, $R_4$ is methyl, $R_5$ is phenyl, $R_6$ is hydrogen, and rings A and B are not further substituted.

6. Process for the manufacture of a colorless color former of the formula

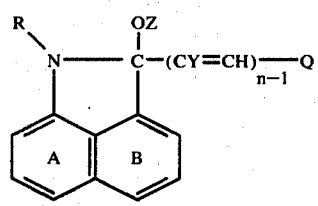

wherein
- R is alkyl with 1 to 6 carbon atoms, cyclohexyl, phenyl, benzyl, 2-phenylethyl or alkyl with 1 to 6 carbon atoms substituted by halogen or alkoxy with 1 to 4 carbon atoms,
- Z is hydrogen or alkyl with 1 to 4 carbon atoms,
- Y is alkyl with 1 to 4 carbon atoms, nitrile or hydrogen,
- $n$ is 1 or 2,
- Q is N,N-disubstituted aniline, indole, naphthol-ether, phenol-ether, phenylpyrazoline or tetrahydrocarbazole, wherein a naphtholactam dyestuff of the formula

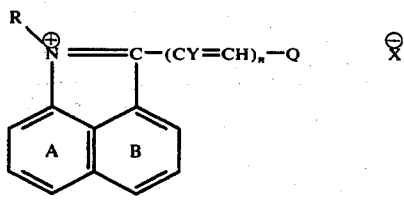

wherein
- $X^\ominus$ is an anion, is treated with a solution of alkali metal hydroxide or alkali metal alkoxide in an amount sufficient to convert said dyestuff into said colorless color former, and recovering said colorless color former.

* * * * *